US00RE35824E

United States Patent [19]

Welker

[11] E Patent Number: Re. 35,824

[45] Reissued Date of Patent: Jun. 16, 1998

[54] FLUID SAMPLE APPARATUS FEATURING INTEGRAL CONSTRUCTION WITH A MOTOR DRIVEN SAMPLING SYSTEM

[75] Inventor: Brian H. Welker, Sugarland, Tex.

[73] Assignee: Welker Engineering Company, Sugarland, Tex.

[21] Appl. No.: 538,040

[22] Filed: Oct. 2, 1995

Related U.S. Patent Documents

Reissue of:

[64] Patent No.: 4,928,536
Issued: May 29, 1990
Appl. No.: 418,522
Filed: Oct. 10, 1989

U.S. Applications:

[63] Continuation of Ser. No. 336,830, Nov. 9, 1994, abandoned.

[51] Int. Cl.[6] ..... G01N 1/14

[52] U.S. Cl. ..... 73/863.83

[58] Field of Search ..... 73/863.51, 863.52, 73/863.81, 864.34, 863.83

[56] References Cited

U.S. PATENT DOCUMENTS

| | | | |
|---|---|---|---|
| 3,704,813 | 12/1972 | Devol | 137/315 |
| 3,945,770 | 3/1976 | Welker | 417/401 |
| 4,346,611 | 8/1982 | Welker | 73/863.86 |
| 4,391,152 | 7/1983 | Ellett | 73/863.84 |
| 4,403,518 | 9/1983 | Welker | 73/864.34 |
| 4,440,032 | 4/1984 | Welker | 73/863.84 |
| 4,470,773 | 9/1984 | Welker | 417/479 |
| 4,481,785 | 11/1984 | Welker | 73/863.84 |
| 4,525,127 | 6/1985 | Welker | 73/863.84 |
| 4,531,895 | 7/1985 | Zeck | 417/401 |
| 4,557,151 | 12/1985 | Welker | 73/863.84 |
| 4,628,750 | 12/1986 | Welker | 73/864.63 |
| 4,631,967 | 12/1986 | Welker | 73/861.25 |

OTHER PUBLICATIONS

Y-Z Industries, Inc., Brite-Rite Model Br-2E, Natural Gas Sampler, Jan. 15, 1986.

Y-Z Industries, Inc., "LPR-2 Light Liquid Hydrocarbon Sampler" Nov. 1985.

Y-Z Industries, Inc., "PNR—2/Probe Mounted Liquid Sample Pump" (date unknown).

Tru-Cut Sampler Systems Model "C" Sries (date unknown).

Y-Z Industries, Inc., "PRN-1 Sampling System" 1981.

*Primary Examiner*—Robert Raevis

*Attorney, Agent, or Firm*—Robert A. Felsman; Mark D. Perdue

[57] ABSTRACT

A fluid motor integrally constructed on an elongate body enables periodic fluid sampling. This device affixes to a pipeline by a threaded connection which positions an inlet in the pipeline for sample removal; the sample flows to a sample bite removal valve which is motor operated to obtain periodic simple bits. Pressure step up or down is achieved in a sample pressure isolation system having a check valve function. This enables storage at any pressure.

21 Claims, 2 Drawing Sheets

65
66

65
64
63
10
30
40
29
36
35
27
28
41
38
33
42
34
24
50
25
49
52
23
53
48
26
47
51
45
20
22
46
60
56
19
59
16
21
18
13
17
58
57
12
11
61
14
15

FLUID SAMPLE APPARATUS FEATURING INTEGRAL CONSTRUCTION WITH A MOTOR DRIVEN SAMPLING SYSTEM

Matter enclosed in heavy brackets [ ] appears in the original patent but forms no part of this reissue specification; matter printed in italics indicates the additions made by reissue.

*This is a continuation of application Ser. No. 08/336,830, filed Nov. 9, 1994, now abandoned, which is a Reissue of 07/418,522, now (surrendered) U.S. Pat. No. 4,928,536.*

BACKGROUND OF THE DISCLOSURE

The present apparatus is directed to an integrated construction of a fluid sampling apparatus and more particularly to one which incorporates a fluid sampling metering mechanism. It is particularly adapted for use with flowing fluids in pipelines of variable pressure. It can be used with a pipeline flow system with pressures as high as necessary for operation of the pipeline, as low as might be encountered, and all pressures in between. It is also intended for use with gases or liquids.

The present inventor has been involved heretofore in various and sundry high pressure pumps, sample collection devices, and devices which insert into a pressure vessel including a pipeline. Such items are exemplified by the following U.S. patents:

3,945,770: HIGH PRESSURE PUMP 4,346,611: INSERTION REGULATOR FOR PRESSURIZED PIPELINES 4,403,518: SAMPLER APPARATUS 4,440,032: SAMPLER INCLUDING A PURGE SYSTEM 4,525,127: VANISHNG CHAMBER CRUDE OIL SAMPLER 4,557,151: SAMPLER INCORPORATING PRESSURE BALANCED CHECK 4,628,750: INTEGRATED PUMP AND SAMPLE VESSEL

These patents as well at the catalog of products of the corporate manufacturer of the devices described thereby represent systems utilized heretofore for obtaining samples from a fluid flow system. It is the purpose of the present disclosure to set forth a fluid sampling apparatus which is an integrated structure having advantages set forth below.

Consider a typical situation involving a fluid flow pipeline which may fluctuate between 500 and 2,500 psi pressure, the fluctuations in part arising from variations in demand. Consider the same situation where the pipeline may deliver natural gas or oil; the sales price for the fluid will fluctuate depending on BTU content, $CO_2$, and other variables. The sample is removed from the pipeline in proportion to flow. It is removed into a storage vessel, and that is periodically carried to a laboratory for testing. The sample must be collected in proportion to the flow and thus, one part per million or one part per billion may be sampled, stored and assayed to determine price. In one example, the BTU per mcf assay is determined and the payment obligations for the natural gas transaction can then be calculated. The same is also true of liquid deliveries. In summary, it is important to obtain measured quantities of sample.

The sample storage container may have an internal pressure which is greater or less than the pipeline pressure. That pressure can vary widely also. Another variable of importance is the portion to be taken to make up the sample. Again, it can vary by perhaps three or four orders of magnitude.

An important factor in the present disclosure is the ease and the facility in which an installation can be made. Briefly, such an installation is often required at remote locations in gas field gathering lines, or perhaps at an intermediate sized pipeline. Such locations are remote and difficult to access. It is difficult to make complex equipment installations in the field. In part, this relates to the difficulty in drilling into the pipeline and forming what is known as a hot tap. Even where the connection is made without the hot tap, it is an expensive undertaking. Cost, complexity and reliability are substantially impacted by the present apparatus. It is more readily installed and installed with a good deal of ease in contrast with the typical system which is assembled in the field with a multitude of components. The present apparatus is characterized as an integrated system which can be attached at a hot tap or alternately in original field installation before the pipeline is placed in service. In either case, the installation process is enhanced by use of an integrated system. Moreover, the integrated system enables fluid flow to be diverted into the equipment, subjected to control by an off/on valve and directed into the system for sampling. More sample is taken out of the pipeline than is required and only a portion thereof is subsequently stored. In other words, the tapped flow is much larger than the sample quantity required and so it is further reduced in volume to match the desired sample output. This is accomplished with pressure isolation. That is, the sample which is delivered at pipeline pressure is isolated for storage at the pressure of the storage vessel. Accordingly, a fluid operated piston with a connected piston rod received in the cylinder is utilized to take timed bites from the removed sample flow. The sample bites are pressure isolated from the pipeline pressure and are delivered to a sampling valve including a check valve and are then delivered out of that apparatus at whatever pressure is necessary to be received in a storage container. Any back pressure encountered is overcome.

The integrally constructed apparatus incorporates a piston and connected piston rod cooperative with a sampling valve. All of this equipment must be properly aligned for installation. By means of integral construction, field alignment is thereby avoided. Further by proper alignment, flow passages through the device are provided so that a small sample flow is derived from the pipeline. The device includes an integrated off/on valve. There are two embodiments of the present disclosure and the one is particularly intended for flowing [gases]. In that embodiment, there are two off/on valves, one for the sample deliver and the other connected in the sample return line so that any surplus sample is returned back to the pipeline.

A [liquid] embodiment is also set forth. The [liquid] embodiment incorporates a similar off/on valve. The [liquid] embodiment is able to remove a [liquid] sample flow which is delivered through a sampling valve and is delivered bite by bite to the sample storage device. The sample storage device is typically a detachable or removable fixed volume container which lends itself to easy removal, transportation to a laboratory and subsequent testing to assay the nature of the sample and to typically obtain the dollar in accordance with some pricing relationship.

The foregoing is directed to some advantages of the present invention but more advantages will be noted and understood on review of the preset disclosure in conjunction with the drawings set forth below.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Figure 1:
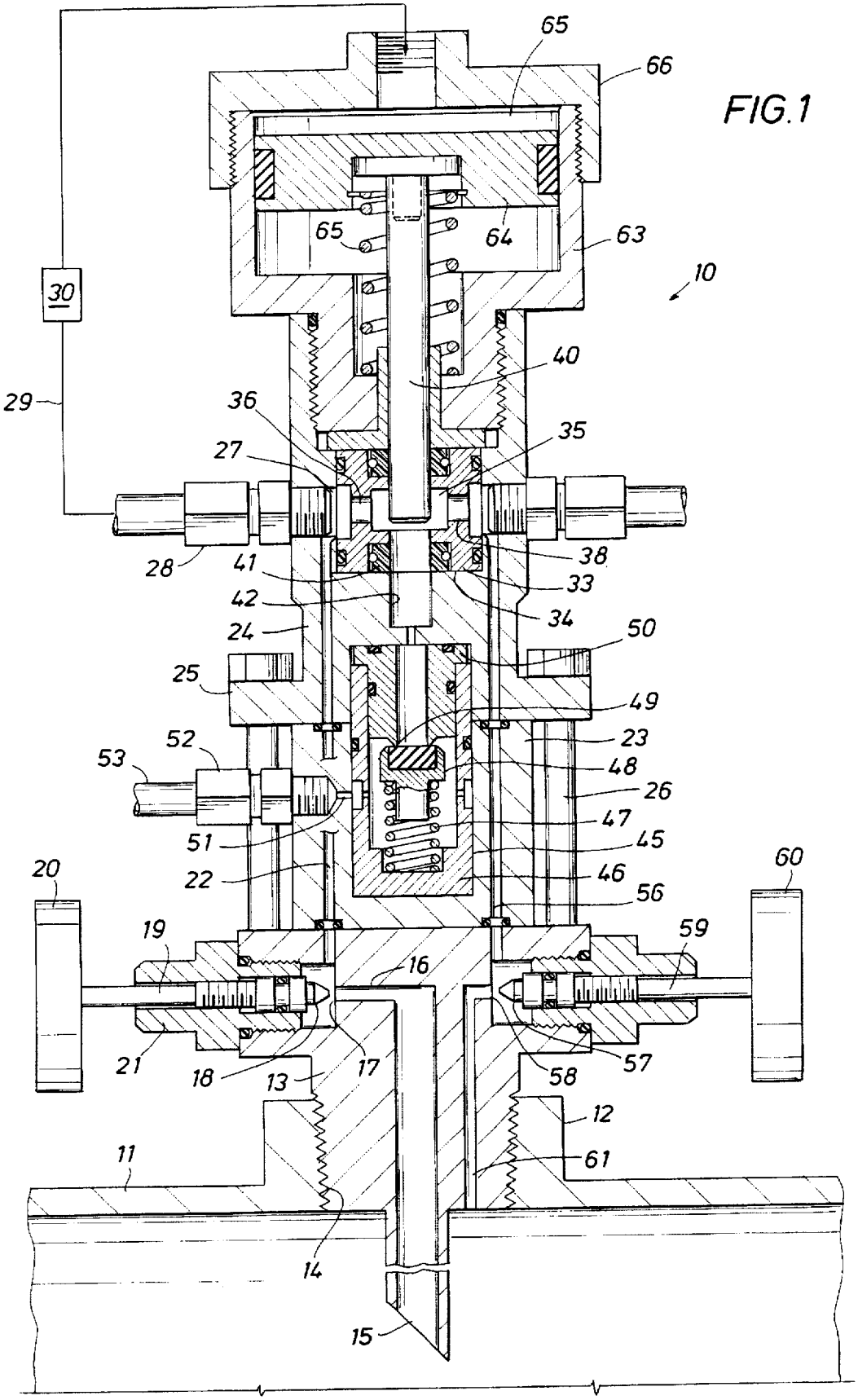
FIGS. 1 and 2 set forth alternate but similar embodiments of the integrally constructed fluid sampling apparatus of the present disclosure.

Attention is first directed to FIG. 1 of the drawings which shows in sectional view a device 10 in accordance with the teachings of the present disclosure particularly intended for use in liquid flow sampling and which device is ideally installed in a liquid flow pipeline. The description will proceed from the bottom, beginning there to describe the fluid intake and extending through the fluid sampling apparatus which is shown herein. FIG. 1 therefore shows the wall of a pipeline at 11 which is provided with an upstanding circular inlet 12 which is axially hollow and internally threaded to join to the sampling apparatus 10. The sampling apparatus incorporates an elongate body made of multiple sections. The lowermost section is identified at 13 and is constructed with a threaded lower periphery 14. This fastens to the pipeline and inserts a liquid inlet opening 15 to a specified depth within the pipeline to assure delivery of a fluid sample. This is connected to a passage 16 extending axially through the body 13. The passage 16 connects with a circular valve seat 17, and the seat is closed by a tapered threaded plug 18 which is a valve element. The plug 18 is mounted on a stem 19 connected with a handle 20. It is axially positioned on the interior of a threaded sub 21 which is threaded to the body 13 and is isolated with a seal ring to prevent leakage along the threads. The axial passage through the center supports the stem 19 which is advanced by rotation. On rotation, the stem positions the valve element 18 in the opening 17 which functions as a valve seat. In turn, fluid flows from the passage 16 and through the valve seat 17 into a supply line 22. The supply line is completely blocked when the valve element 18 is advanced against the valve seat 17. The valve thus functions as a supply on/off control. Metering of the flow is obtained by the valve element.

The sampler 10 is constructed of the first body portion 13. A second body portion 23 is also included. It is an elongate cylindrical body portion having passages drilled therein as will be described, and this body portion extends to and connects with the next body portion 24. In turn, the several body portions are held together so that there is no leakage. They are preferably fabricated with parallel faces, the end faces being joined with appropriate seals. Moreover, a flange 25 extends radially outwardly from the body portion 24 and suitable bolts 26 thread through the flange 25 and into the portion 13. This captures the cylindrical body portion 23 therebetween and applies pressure to the seals.

Assuming the valve 18 is in the open position, fluid flows through the supply passage 22 and then to a tee 27. One leg of the tee is through the fitting 28, line 29 and a control valve 30. The line 29 extends to the upper end of the sampler 10 and is used in a fluid motor to be described. The tee 27 is defined by positioning an insert 33 within the body 24, the body 24 being substantially hollow. The insert 33 is positioned internally against a registration shoulder 34 and is provided with internal and external seals to prevent leakage around the outer surface thereof. The insert 33 has an internal fluid receiving chamber 35 which is a sample receiving chamber. It connects with the tee 27 by means of the port 36. The port 36 is an inlet port through the insert 33 to the chamber 35, and there is additionally an outlet port 38 which is symmetrically constructed through the insert 33. A plunger 40 extends into the chamber 35 and is sized to pass through the chamber 35 and to sealingly engage a seal member 41 held in position by the insert 33. The plunger reciprocates downwardly, forcing fluid into a passage 42, the fluid flowing through the passage 42 when the plunger moves. Fluid in the passage 42 is trapped. It is a specified bite of fluid which is sized by the dimensions of the passage 42. The passage 42 is axially communicated with an enlarged chamber 45 which receives a cylindrical insert 46. The insert 46 functions as a spring cage to position a compressed coil spring 47 bearing against a valve element 48. The valve element 48 is constructed with a central resilient plug. That plug seats against the valve seat 49 formed at the lower end of a telescoping insert 50. The insert 50 nests within the cage 46 to position the valve seat 49 in operating relationship to the insert 48. Moreover, the insert 50 is hollow, delivering fluid from the passage 42 through the valve seat. With the valve 48 against the seat, no flow occurs. Flow occurs when the pressure bearing against the valve element 48 is sufficient to force the valve open against the force of the spring 47. Moreover, fluid which flows past the valve then is delivered to a fluid outlet passage 51 through appropriate fittings 52 and a conduit 53 for delivery of fluid to a remote sample storage container.

Returning to the plunger 40, it will be observed that the plunger isolates a certain portion of liquid for delivery through the passage 42. A portion of the liquid does not flow into the passage. Rather, the sample which is delivered through the sample supply line 22 is directed through the insert by flowing first into the passage 36 and out through the passage 38. Flow through the passage 38 is delivered to a surplus fluid line 56 extending downwardly in FIG. 1. This fluid flows to an outlet valve which is defined by a valve element 57 operatively positioned opposite a valve seat 58. The valve element 57 is mounted on a threaded stem 59 having a handle 60 for opening and closing of the valve. Moreover, fluid is delivered into a return passage 61 for return into the pipeline.

The fluid flow paths include the following routes. All fluid that is introduced into the sampler 10 flows upwardly through the passage 16. As will be understood the direction of flow in the pipeline is from left to right as viewed in FIG. 1 and the shape of the inlet 15 directs fluid upwardly into the passage 16. The equipment can be switched off by closure of the valve handle 20. It is, however, normally switched on by opening the valve by rotation of the handle 20. This separates the valve element 18 from the valve seat 17 and permits fluid to flow upwardly through the passage 22. This passage extends upwardly to the tee 27 and delivers fluid into the passage 42. When the plunger 40 is in the up position, fluid will flow through the tee 27 and out through the passage 38. The surplus fluid passage then delivers the surplus fluid through the return control valve operated by the handle 60. Surplus fluid is delivered through the line 61 back into the pipeline.

The spring 47 is selected and sized so that its spring force exceeds the pressure experienced at the valve element 48. Thus, the valve element is a check valve which is closed at all times except on operation of the plunger 40. Thus, if pipeline pressure is 2,000 psi, then the spring 47 is sized so that the check valve does not open at this pressure to deliver a sample out of the system. The spring is sized to require a greater pressure for closure. On the other hand, when the plunger 40 reciprocates downwardly to raise pressure in the passage 42, the plunger 40 force raises the pressure sufficiently that the check valve is overcome, and fluid is delivered to the sample outlet means 53. This conveys the outlet fluid downstream to the sample collection apparatus. Moreover, the sample collection apparatus may have substantial pressure and hence create back pressure at the outlet means which must be overcome. Whether the back pressure is high or low, the plunger 40 has a stroke of sufficient length below the seal 41 to force a specified volume of sample out of the sample flow and deliver it into the sample collection apparatus notwithstanding any back pressure encountered.

Consider the relative size of the sample relative to the fluid flow. For a particular pipeline operating pressure, pipeline diameter, and liquid velocity through the pipeline, liquid is delivered at a specified rate. By sizing the inlet opening 15 relative to the pipeline and positioning it at a specified depth in the pipeline, fluid is delivered into the sample inlet line 22 in a specified ratio relative to pipeline flow. This ratio can be some arbitrary value such as one unit per 10,000 units of flow. That sample is delivered past the plunger 40 which periodically takes a bite. The bite which is removed is sized relative to the flow moving past the plunger 40. The flow fills the passage 42 prior to operation of the plunger 40. When the plunger enters the seal 41 and closes off that chamber, a specified volume of sample is forcibly displaced by plunger movement. That volume is forced through the check valve and into the sample storage apparatus. This is a specified ratio dependent in part on the flow rate of sample moving past the plunger 40, the size of the chamber 42, the length of the plunger stroke, and other appropriate scale factors. It is desirable to have a fixed sampling rate such that the sample actually removed and delivered to the storage container in one part per 100 units, or as much as one part per 10,000 units. Again, this is a scale factor and it can be controlled by changing the size of the plunger 40, changing the length of plunger stroke, and also by changing the frequency or interval at which the plunger is operated. In any event, that ratio is implemented, and for purposes of description, assume that it is one unit of sample for 1,000 units of flow through the sampling mechanism 10. The plunger thus removes a portion for subsequent testing. Since only a portion of the flow is taken by the inlet means 15 and the sampling valve means 40 takes only a portion, the two ratios are multiplied together to obtain a sampling ratio. The sampling ratio can be anywhere between $10^5$ to about $10^9$. These are representative scale factors which can be implemented by scaling the equipment in the fashion described. Moreover, this ratio preferably is established at the time of installation of the present apparatus or in the event of subsequent change in the nature of the product being sampled. In that instance, it may be necessary to change sizes of components. For instance, the spring 47 might be changed in size. The plunger stroke can be adjusted also. Alternately, frequency of operation by the controller 30 can be implemented.

Continuing with the description of FIG. 1, the upper end of the sampler incorporates a cylinder attachment 63. It encloses a piston 64 which is connected to the plunger 40. The piston 64 is a single acting piston, and it is returned to its initial position by means of a return spring 65. The return spring 65 is seated on a shoulder counter bored into the cylinder attachment. The piston defines a fluid receiving chamber 65 which is on the top side of the piston. Moreover, the top end of the equipment is closed by a cylinder head 66 which threads to the cylinder attachment 63 and thereby defines the chamber 65. Fluid which is delved into the chamber 65 is also vented back through the feedline and is controllably disposed of by the controller 30. Venting is accomplished by controller 30 shutting off flow from line 29 and then venting the fluid in the line and chamber 65 to the atmosphere or other low pressure area.

The system utilizes pipeline pressure which is delivered to the top of the piston 64. This large area piston assures that the force applied to the plunger 40 is sufficient to overcome the spring 65 and to compress the liquid captured by the plunger during operation. Moreover, the plunger is driven downwardly by a specified stroke. Thus assures that the plunger takes a consistent and equal sized bite during operation. It forces captured liquid out of the passage 42 past the check valve in the quantity determined by the diameter of the plunger 40 and the length of its stroke past the seal 41.

DETAILED DESCRIPTION OF THE GAS EMBODIMENT

Figure 2:
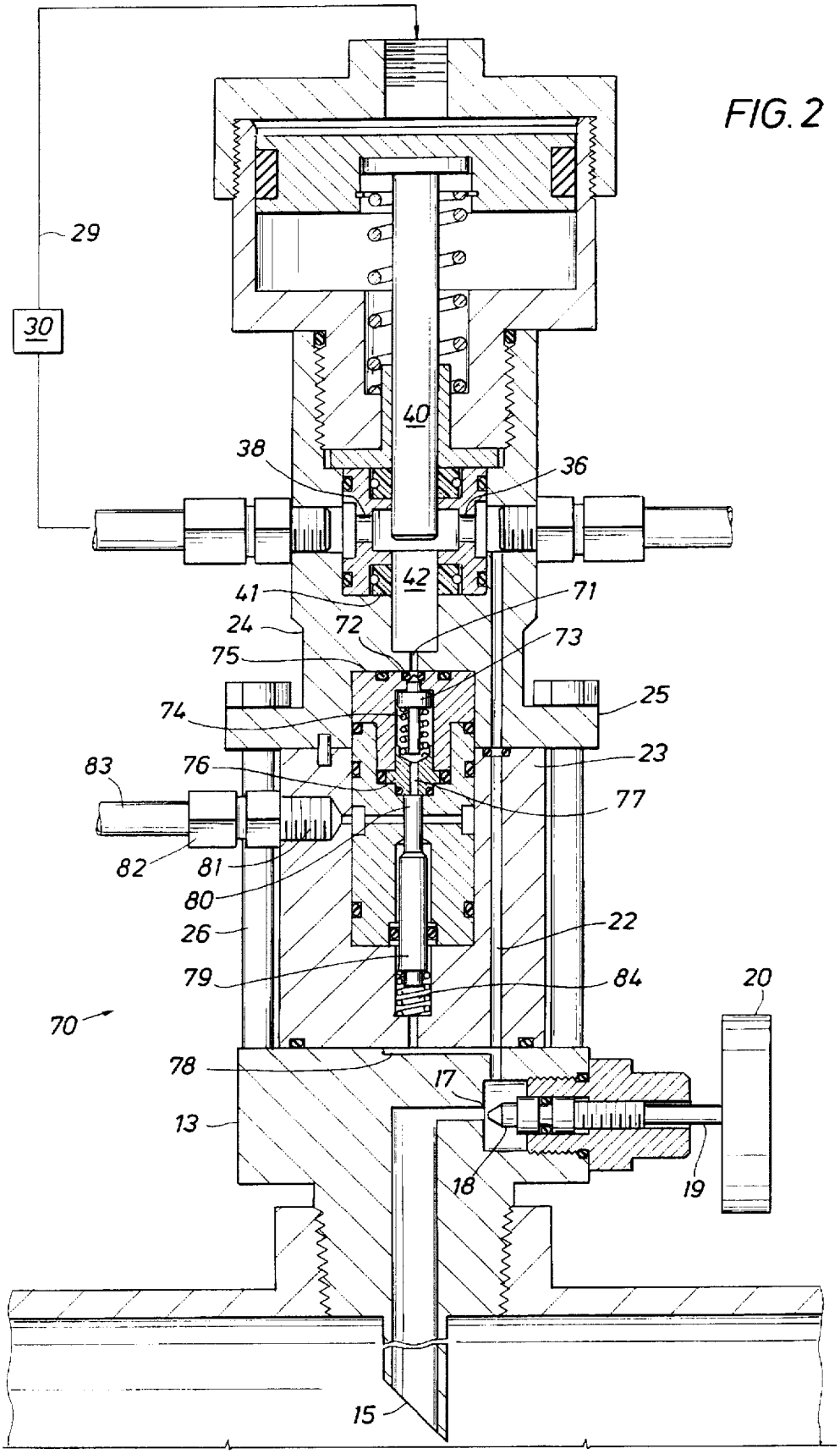

Going now to FIG. 2 of the drawings, an alternate embodiment is illustrated in sectional vie. The numeral 70 identifies an alternate structure which is constructed for handling gaseous products, typically natural gas, and which is constructed in similar fashion to the structure shown in FIG. 1. A substantial portion of the description remains the same. Accordingly, the lower portion 13 again is identified by the same reference numeral as before. It is joined to a cylindrical portion 23 thereabove of similar construction. The structure includes the same flow inlet at 15 which is delivered to a similar valve seat 17 cooperating with a similar valve element 18 which is stem supported by a similar stem 19 and which is opened and closed by a similar handle 20. This apparatus has been illustrated at the right side of FIG. 2, but it will be appreciated that it is structurally the same as the structure shown on the left of FIG. 1. For clarity in the drawings, it is illustrated on the right so that the flow line 22 is shown in a less obscure position. In like fashion, the sampler 70 includes the intermediate body portion 24 which again is joined by the bolts 26 extending through the flange 25 thereabove. The fluid flow is delivered for compression by a similar plunger 40. That is, the inlet from the pipeline is through the passage 22 and that is directed through the port 36 and out through the port 38. These ports again are shown on opposite sides of the drawing but they are identical to those shown in FIG. 1. Fluid for operation of the fluid motor is delivered through the supply line 29 and the timed controller 30 is again illustrated for timed operation of the fluid motor in the sampler 70.

The plunger 40 again pumps downwardly through a seal 41 which encircles the plunger and thereby defines a downwardly extending a passage or chamber 42. That terminates at [a] *rigid* relatively narrow passage 71 which opens to a valve seat 72 defined by a resilient O-ring. There is a tapered needle valve element 73 positioned against the seat. It incorporates a needle valve tip for guidance, and it is forced open by gas flow against the valve element 73. The needle valve is urged to a closed position by resilient spring 74. The spring is captured below a spring mechanism, this mechanism including a surrounding insert 75, a captured orifice fitting 76, and suitable seals to prevent leakage around these components. Gas flows from the chamber 42 through the small orifice 71. It flows through the needle valve and past the needle valve. It flows through a small orifice passage 77 drilled in the orifice fitting 76. It is delivered through the bottom of this passage and out that opening. However, fluid is not permitted to flow because there is a pressure set check valve to be overcome. This pressure set check valve is made dependent on line pressure. Specifically, line pressure is introduced from the supply passage 22 through a lateral line 78, and below a plunger 79. The plunger 79 supports a plug 80 which blocks flow out through the passage 77. The plug 80 is smaller than the passage and hence, any gas flow escaping that contact flows downwardly and into the port 81 when contact between plug 80 and fitting 76 is broken. The port 81 includes the appropriate fittings 82 and connects through the outlet line 83 to a sample storage container. The plunger 79 is forced upwardly by a bias spring 84 which is of sufficient strength to force the plug 80 upwardly. However, plug movement is controlled primarily by the cross-sectional area of the plunger 79 and pressure which is exposed to it. Representative pressure levels will be given hereinafter.

Consider a typical situation in operation. Assume that the sampler 70 is installed on a natural gas line at 1,000 psi. Fluid flows from left to right as viewed in FIG. 2. The inlet means 15 draws in fluid flow, and it flows into the inlet passage 22 assuming the valve handle 20 has been operated to open the valve 18. This fluid flows to the plunger 40. It is captured in the passage 42 when the plunger is operated downwardly. Surplus fluid is delivered away from the plunger. One outlet is through the line 29 which flows to the timed controller 30 which times application of fluid to the fluid motor at the top end which operates in the same fashion as shown in FIG. 1 of the drawings. That is, the plunger 40 is driven downwardly by the piston, and compression of the captured gas occurs in the passage 42. *As can be seen in FIG. 2, fluid or gas from the pipeline and rigid sample chamber 42 is employed (through passage 38, line 29, and controller 30) to actuate plunger 40, and the volume of gas sampled after actuation of plunger 40 is fresher or more representative of that flowing in the pipeline at the time of the sample.*

The gas is compressed, forced downwardly, and the flows past the needle valve. It flows into the small passage 77 through the orifice insert 76. When this pressure is sufficiently high, it will force the plug 80 slightly downwardly so that gas flows around the plug 80. Gas flows through the outlet port or passage 81 into the fitting 82 and through the line 83 for delivery to the sample storage chamber which is not shown. The gas so stored is recovered for sample testing purposes.

Consider representative pressures which might occur in the sampler 70. The passage 78 is provided with gas at line pressure or 1,000 psi in this example. It is applied below the plunger 79. The plunger 79 has a ratio of area to the plug 80 of about 2:1 and provides multiplication of approximately two fold in that event. That is, gas samples delivered through the passage 77 must exceed approximately two fold line pressure. In other words, the plug 80 will not open until pressure bearing against it at the top end is in excess of about 2,000 psi in this example. Gas flows upwardly through the supply passage 22 and is delivered into the chamber 42. When the plunger 40 moves downwardly into the seal 41, pressure rises in the chamber 42. This pressure rise is observed therebelow in the passage 77. When that pressure becomes sufficient, the plug 80 is forced backwardly, opening slightly and gas flows into the port 81. Fluid then flows while exceeding this representative pressure. That is, the gas that is delivered through the outlet line 83 is compressed to a sufficient pressure that is forces open the tapered needle valve 73, and also flows past the plug 80.

Assume that the storage container for the sample is maintained at a pressure which is low. In that event, the sample is simply delivered in regular fashion into that storage vessel. If however, the back pressure of the storage vessel is much greater than the line pressure, that does not pose any problem either. Sample cannot escape back into the equipment because there is a check valve at the valve 73. Accordingly, the pressure on the compressible gas is raised sufficiently high that it will overcome practically any back pressure at the storage container. Moreover, pressure is isolated between strokes so that the storage container does not bleed through the sampling valve just described.

Consider proportioning of the present apparatus. Sample again is captured in the range of about one part in $10^5$ up to about one part in $10^9$. Obviously, these are subject to scale factors and can be varied to a desired output sampling rate.

The samplers 10 and 70 utilize the same basic structural components. They both terminate at a remote end which incorporates a fluid motor. In both instances, the motor is preferably single acting with a return spring. That is, fluid pressure from the pipeline is used to drive the piston. This avoids the necessity of providing a remote fluid supply at a remote location. Just as importantly, pipeline pressure is not a limitation on the operation of the fluid motor because it is provided with greater cross-sectional area so that even a low pipeline pressure system can provide sample against a high back pressure storage device.

While the foregoing is directed to the preferred embodiment, the scope thereof is determined by the claims which follow:

What is claimed is:

1. An assembly for obtaining a fluid sample from a pressurized pipeline comprising:

(a) an elongate body having (i) a first end formed to connect to a pipeline to position a pressurized fluid inlet *probe* in the pipeline to receive pressurized fluid;

(ii) a central body portion connected to said first end; and (iii) a second end deployed from said first end;

(b) a fluid flow *inlet* line *extending through said elongate body and* connected from said fluid inlet *probe* to deliver a flow of fluid;

(c) fluid sampling means connected to said fluid flow *inlet* line [to deliver fluid thereto] *such that fluid is delivered to said fluid sampling means* in a volume in excess of said sample, *said sampling means periodically removing fluid from said fluid flow inlet line*;

(d) [said sampling means periodically removing fluid from said fluid flow line;

(e)] outlet means connected to said sampling means for delivery of a fluid sample [without regard to] *whether* the pressure in the pipeline *exceeds that in a fluid sample vessel or the pressure in the fluid sample vessel exceeds that in the pipeline*;

[(f)] (*e*) check valve means cooperative with said outlet means to enable fluid to flow through said outlet means to overcome back pressure encountered by fluid flow;

[(g)] (*f*) *said fluid sampling means including a* rigid *sample* chamber connecting means connecting said *fluid* sampl[e]*ing* means and check valve means; and

[(h)] (*g*) motor means in said body for operating said sampling means to direct fluid through said outlet means, *said motor means being in fluid communication with the pipeline through said fluid sampling means,*

*wherein, upon actuation of said motor means and said fluid sampling means, a fresh sample of pressurized fluid from the pipeline is taken.*

2. The assembly of claim 1 wherein said fluid sampling means comprises:

(a) [sample chamber means for receiving pressurized fluid therein;

(b)] a movable plunger sealingly received in said *rigid sample* chamber means;

[(c)] *(b)* means connecting said motor means to said plunger to reciprocate said plunger through a first position to allow fluid in said chamber means, and reciprocate said plunger to a second position to force fluid through said check valve means; and

[(d)] *(c)* said motor means forms sufficient pressure to open said check valve means and also overcome any back pressure encountered by fluid flow from said outlet means.

3. The assembly of claim 1 wherein said elongate body is formed by:

(a) a lower end portion having a downwardly extending probe for insertion into a pipeline, and said probe extends from a threaded fitting cooperatively connecting to a mating fitting on the pipeline;

(b) an intermediate portion supporting said outlet means and said check valve means; and (c) an upper end portion comprising said second end and supporting said motor means wherein said upper end portion is joined with and connected to said intermediate portion to align sad body portions for joinder in an integrated assembly.

4. The assembly of claim 3 *further* including *at least one fluid flow* passage[s] extending through *each of* said body portions for controlled fluid flow from said fluid inlet and to said outlet means as controlled by said fluid sampling means and said check valve means.

[5. The assembly of claim 4 wherein said passages include:

(a) an inlet flow passage to said fluid sampling means;

(b) an outlet flow passage from said fluid sampling means for delivery of surplus fluid not sampled by said sampling means, said outlet flow passage having a separate outlet for the surplus fluid.]

6. The assembly of claim [5] *4* wherein said outlet flow passage is directed to said lower end body portion and said outlet thereof returns surplus fluid into the pipeline.

7. The assembly of claim 3 wherein said motor means comprises a piston in a cylinder defining a fluid receiving compression chamber, and said piston is connected to a plunger moveably positioned in a chamber to reciprocate, said plunger and chamber comprising said fluid sampling means.

8. The assembly of claim 1 wherein said fluid sampling means and said check valve means comprise:

(a) a reciprocating plunger;

(b) a fluid receiving chamber for receiving fluid therein, said chamber further receiving said plunger to force fluid out of said chamber;

(c) a passage for pressurized fluid from said chamber;

(d) a valve seat fluidly connected to said passage;

(e) a valve element cooperative with said valve seat to close said passage to fluid flow; and (f) spring means bearing against said valve element to provide a force overcome by fluid pressure on operation of said plunger, said spring means otherwise closing said valve element.

9. The assembly of claim 8 wherein said valve element is a needle valve.

10. The assembly of claim 9 including an additional serially connected supply pressure operated valve means closing as a function of pipeline pressure.

11. The assembly of claim 8 wherein said valve element is a resilient plug larger in size than said valve seat and is constructed to fully close off fluid flow.

12. The assembly of claim 11 wherein said resilient plug is supported in a surrounding metal ring.

13. The assembly of claim 12 wherein said ring includes a connected stem mounting said resilient plug for reciprocation.

*14. An assembly for obtaining a fluid sample from a pressurized pipeline comprising:*

*(a) an elongate body having*

*(i) a first end formed to connect to a pipeline to position a pressurized fluid inlet probe in the pipeline to receive pressurized fluid;*

*(ii) a central body portion connected to said first end; and*

*(iii) a second end deployed generally opposite from said first end;*

*(b) a fluid inlet passage extending from said pressurized fluid inlet probe and through said elongate body to deliver fluid from said pipeline in a volume in excess of said fluid sample;*

*(c) fluid sampling means disposed in said elongate body and defining a rigid sample chamber connected to said fluid inlet passage to receive fluid from said pipeline through said fluid inlet passage, said sampling means periodically removing said fluid sample from said fluid inlet passage;*

*(d) a fluid outlet disposed in said elongate body and connected to said rigid sample chamber of said fluid sampling means for periodic and selective delivery of said fluid sample to a sample storage vessel;*

*(e) a first check valve disposed in said elongate body and cooperative with said fluid sampling means to prevent fluid flow from said sample storage vessel past said fluid sampling means when pressure in said sample storage vessel exceeds pressure in said pipeline;*

*(f) a second check valve disposed in said outlet and said elongate body and in fluid communication with said fluid sampling means to permit said selective and periodic delivery of said fluid sample to said sample storage vessel when pressure in said pipeline exceeds pressure in said sample storage vessel, said second check valve being in fluid communication with said pipeline exclusively through passages formed in and through said elongate body; and*

*(g) a motor in said body for operating said sampling means to direct fluid through said outlet and into the sample storage vessel.*

*15. The assembly of claim 14 wherein said fluid sampling means comprises:*

*(a) a movable plunger sealingly received in said rigid sample chamber;*

*(b) means connecting said motor to said plunger to reciprocate said plunger though a first position to allow fluid into said rigid sample chamber, and reciprocate said plunger to a second position to force fluid through said second check valve; and*

*(c) said motor forming sufficient pressure to open said second check valve and also overcome any back pressure encountered by fluid flow in said outlet.*

*16. The assembly of claim 14 wherein said elongate body is formed by:*

*(a) a lower end portion having a downwardly extending probe for insertion into a pipeline, and said probe extends from a threaded fitting cooperatively connecting to a mating fitting on the pipeline;*

*(b) an intermediate portion supporting said outlet and said check valves; and*

*(c) an upper end portion comprising said second end and supporting said motor means wherein said upper end portion is joined with and connected to said intermediate portion to align said body portions for joinder in an integrated assembly.*

*17. The assembly of claim 14 wherein said motor comprises a piston in a cylinder defining a fluid receiving compression chamber, and said piston is connected to a plunger movably positioned in said rigid sample chamber to reciprocate, said plunger and rigid sample chamber comprising said fluid sampling means.*

*18. The assembly of claim 14 wherein said fluid sampling means comprises:*

*(a) a reciprocating plunger;*

*(b) said rigid sample chamber receiving said plunger to force fluid out of said chamber;*

*(c) a passage for pressurized fluid from said rigid sample chamber to said outlet.*

*19. The assembly of claim 18 wherein said first check valve comprises:*

*(a) a valve seat fluidly connected to said outlet;*

*(b) a valve element cooperative with said valve seat to close said outlet to fluid flow; and*

*(c) spring means bearing against said valve element to provide a force overcome by fluid pressure on operation of said plunger, said spring means otherwise closing said valve element.*

*20. The assembly of claim 19 wherein said valve element is a needle valve.*

*21. The assembly of claim 14 wherein said second check valve is a pressure-set check valve in fluid communication with pipeline pressure through said fluid flow inlet passage.*

*22. The assembly of claim 14 wherein the motor is in fluid communication with the fluid sampling means and pipeline, wherein fluid from the pipeline acting upon the motor means passes through the fluid sampling means.*

* * * * *